United States Patent
Staley

(10) Patent No.: US 6,245,942 B1
(45) Date of Patent: Jun. 12, 2001

(54) REDUCTION OF THE CARBONYL VALUE OF CARBOXYLIC ACIDS AND DERIVATIVES OF CARBOXYLIC ACIDS AND DERIVATIVES OF CARBOXYLIC ACIDS

(75) Inventor: Michael D. Staley, Cincinnati, OH (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/258,229

(22) Filed: Feb. 26, 1999

(51) Int. Cl.$^7$ .................................................. C07C 51/42
(52) U.S. Cl. ........................ 562/608; 562/485; 562/593; 562/580
(58) Field of Search .................... 562/416, 487, 562/413, 483, 486, 485, 580, 593, 608

(56) References Cited

U.S. PATENT DOCUMENTS 5,344,969 * 9/1994 Iwane et al. .
5,481,033 * 1/1996 Alms et al. .

OTHER PUBLICATIONS

Database WPI, Section Ch, Week 199808, Derwent Publications Ltd., London, GB, Class D21, AN 1998–082614, XP002141379 & JP 09 316043 A (Kao Corp), Dec. 9, 1997, Abstract.

Database WPI, Section Ch, Week 198409, Derwent Publications Ltd., London, GB, Class A41, AN 1984–054362, XP002141380 & SU 1 011 624 A (Geor Oil Res Inst), Apr. 15, 1983, Abstract.

Database WPI, Section Ch, Week 198511, Derwent Publications Ltd., London, GB, Class A41, AN 1985–066575, XP00214381 & PT 78 759 A (Badische Corp), Jan. 31, 1985, Abstract.

Database WPI, Section Ch, Week 197716, Derwent Publications Ltd., London, GB Class D23, AN 1977–28503Y, XP002141382, & SU 234 585 A (Kuib Aviation Coll), Sep. 29, 1976, Abstract.

Hein et al., Ion–Exchange Resin Catalysis of the Knoevenagel Condensation of Ketones, J. Org. Chem. 26, 4874–4878 (1961).

* cited by examiner

Primary Examiner—Paul J. Killos
(74) Attorney, Agent, or Firm—John E. Drach; Jeffrey S. Steen

(57) ABSTRACT

A method for reducing the carbonyl value of a composition containing carboxylic acid or carboxylic acid derivative includes contacting the composition containing carboxylic acid or carboxylic acid derivative with an amount of a catalyst and active methylene compound effective to lower the carboxyl value of the composition.

20 Claims, No Drawings

REDUCTION OF THE CARBONYL VALUE OF CARBOXYLIC ACIDS AND DERIVATIVES OF CARBOXYLIC ACIDS AND DERIVATIVES OF CARBOXYLIC ACIDS

BACKGROUND

1. Field of the Invention

This invention relates to reduction of carbonyl values in compositions containing carboxylic acids, derivatives of carboxylic acids or both.

2. Description of Related Art

Carboxylic acid and carboxylic acid derivative containing compositions have a multitude of uses as intermediates in the production of materials and as final products. Various processes have been used to produce carboxylic acids and derivatives thereof. These products are then stored or subject to further processing. The processing and storage of these products can result in degradation of the carboxylic acids and contamination of the products. For example, production of azelaic acid or pelargonic acids by ozonolysis of oleic acid is known to lead to a mixture of oxidation products containing carboxylic acids and carbonyl-containing species such as aldehydes and ketones. The presence of aldehydes and ketones may be considered undesirable since they may impart discoloration, odors and tastes to such products. Indeed, processing and storage of fatty acids and derivatives of fatty acids may lead to aldehyde and ketone degradation products resulting from oxidation.

The combined concentration of aldehydes and ketones is known interchangeably as the carbonyl content or carbonyl value. In the present context, the carbonyl value is also a measure of oxidation and may be expressed as milligrams of carbonyl functionality per gram of sample. Carbonyl value is abbreviated COV and may also be expressed in parts per million.

Since aldehydes, ketones and oxo-carboxylic acid derivatives thereof may be considered undesirable contaminants in compositions containing carboxylic acids and derivatives thereof, certain processes have been developed to lower the COV. Typically, keto-acids and aldo-acids are contaminants which are difficult to remove from the carboxylic acid end products, especially on industrial scales. One removal process involves reaction of ketones and aldehydes with oxygen in the presence of a metal ion catalyst such as cobalt and manganese. Unfortunately, treatment with oxygen may result in degradation of the product and toxic manganese or cobalt waste products. The presence of manganese or cobalt in waste streams can present environmental problems.

Consequently, there exists a need for methods of lowering COV, but which eliminates the need for manganese compounds and oxygen for the removal of aldehydes and ketones.

SUMMARY OF THE INVENTION

A process is provided for lowering the carbonyl value of a composition containing carboxylic acid or carboxylic acid derivative which includes contacting the composition containing carboxylic acid with an amount of a catalyst and an active methylene compound effective to lower the carbonyl value of the composition.

Also provided is a process for reducing the amount of carbonyl group containing impurities in a composition which includes carboxylic acid or carboxylic acid derivative, the process including contacting the composition containing carboxylic acid or carboxylic acid derivative with an amount of a catalyst and an active methylene compound effective to form a condensate and to reduce the carbonyl value of the composition and separating the condensate from the composition.

DETAILED DESCRIPTION OF PREFERRED EMBODIMENTS

The present invention provides an efficient, environmentally friendly method of lowering the amount of certain undesirable contaminants in compositions including carboxylic acid and derivative of carboxylic acid without degrading the compositions. As a result, stable carboxylic acid containing compositions are facilitated which have reduced amounts of undesirable colors, odors, tastes and other unwanted properties attributable to such contaminants. The present invention eliminates the need for manganese or cobalt compounds and oxygen for removal of aldehydes and ketones including oxo-carboxylic acids from other carboxylic acid which leads to higher product yields through the reduction of manganese or cobalt soaps and product degradation from oxygen sparging. It should be understood that use of the terms "carboxylic acid" or "carboxylic acid derivative" herein is meant to encompass both singular and plural species, i.e., one or more carboxylic acid molecules or one or more carboxylic acid derivative molecules.

It is contemplated that any carboxylic acid or carboxylic acid derivative containing composition may be subjected to decontamination according to the present invention. The composition may consist entirely of carboxylic acid and/or derivative of carboxylic acid, or the composition may contain other chemical entities. Such carboxylic acid include any carboxyl group containing compound such as saturated and unsaturated aliphatic carboxylic acids, unsaturated and saturated aromatic carboxylic acids and mixtures thereof, e.g., $C_4$ monoacids to $C_{20}$, saturated or $C_{12}$ to $C_{20}$ unsaturated, fatty acids and the like. Diacids, triacids, etc. are also contemplated. It is also contemplated that compositions containing derivatives of carboxylic acids can be decontaminated according to the present invention. Such derivative of carboxylic acid are compounds that yield carboxylic acid upon reaction with water and include acid halides, acid anhydrides, esters, amides, and nitrites.

Reduction of the carbonyl value of a composition containing carboxylic acid or carboxylic acid derivative is achieved by contacting such a composition with a catalyst and an activated methylene compound. Without wishing to be bound by any theory, the reaction appears to involve Knoevenagel condensation which is the reaction of an aldehyde or ketone with a compound that has a hydrogen alpha to two activating groups (such as C=O or C≡N) using a catalyst to form a condensate, i.e., two molecules combine into a larger molecule. Ketones are typically less reactive than aldehydes and more acidic compounds such as active methylene compounds are preferred to facilitate condensation of ketones. Examples of such methylene compounds are provided below. While reference has been made to Knoevenagel condensation herein, the carbonyl value may actually be lowered by formation of undefined products. Suitable catalysts for use in accordance with the present invention include amine, ammonia, ammonium salt, titanium tetrachloride ($TiCl_4$) and aluminum oxide ($Al_2O_3$) or combinations thereof. Suitable amines include primary amines and secondary amines including alkyl amines, arylamines, arylakylamines and the like. A preferred amine is n-octylamine.

Active methylene compounds are well-known in the art. Any compound having the formula $X-CH_2-Y$ wherein X and Y may be the same or different and are electron withdrawing groups is suitable for use herein. Examples of suitable X and Y substituents may be represented by the following formulas:

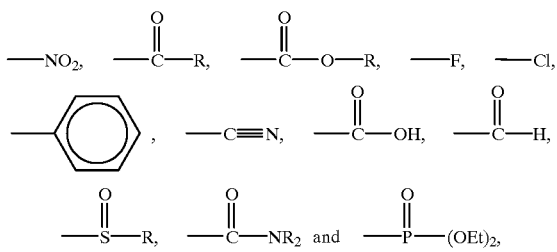

wherein R is alklyl or aryl. Common names of suitable active methylene compounds include malonitrile, benzoylacetonitrile, 2,4-dimethylbenzoylacetonitrile, pivaloylacetonitrile, cyanoacetamide, p-nitrophenylacetonitrile and p-cyanophenylacetonitrile. Particular examples include:

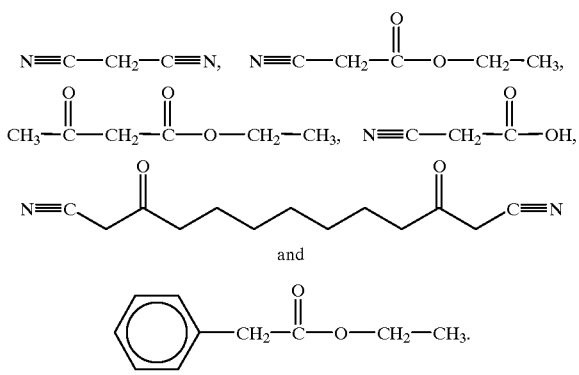

Particularly preferred are cyanoactive methylene compounds such as cyanoacetic acid and ethylcyanoacetate.

The amounts of catalyst and active methylene compound to be added to a composition containing carboxylic acid or carboxylic acid derivative depends on the COV of the composition. For example, the greater the COV, the higher the relative amount of methylene compound and catalyst. Those with skill in the art can determine appropriate amounts of methylene compound and catalyst based upon COV. For example, the amount of catalyst can be greater than about 0.001% by weight of the entire composition and is preferably about 0.01 wt % to about 10 wt % and more preferably about 0.01 wt % to about 0.5 wt % of the composition. The amount of active methylene compound may generally be greater than about 0.1 molar equivalent and is preferably about 0.1 molar equivalent to about 6 molar equivalents and more preferably about 1.5 molar equivalents to about 4 molar equivalents.

Temperatures for the reaction may range from about 0° C. to about the boiling point of the composition regardless of pressure. Preferable temperatures range from about 10° C. to about 150° C. and more preferably, from about 20° C. to about 125° C.

Thus, in one aspect, an active methylene compound and a catalytic amount of catalyst is added to a liquid mixture of carboxylic acid or carboxylic acid derivative containing aldehyde and/or ketone contaminants in a container. It is believed that carbonyl groups of the contaminants react with the active methylene compound and catalyst to form a condensate which is then separated from the desired carboxylic acid or carboxylic acid derivative. Any method of separating the condensate from the desired product known to those skilled in the art is contemplated. For example, distillation is typically effective in separating the desired product from the condensate, leaving the condensate in the container. Other examples of separation methods include chromatographic techniques including HPLC, reverse-phase HPLC, thin layer chromatography, simulated moving bed chromatography, density gradient techniques and the like.

In another aspect, the active methylene compound is bound to a support such as polystyrene resin, Sephadex™ and the like by any method known to those with skill in the art. For example, the methylene compounds may be linked to such support using commercially available homofunctional or heterofunctional crosslinking agents known to those skilled in the art. For example, crosslinkers include imidoesters and N- esters, maleimides, alkyl halides, aryl halides, α haloacyls, carbodiimides and the like. The catalyst is then added to a feed stream containing carboxylic acid and carboxylic acid derivative and contaminants. As the feed stream passes the bound active methylene compound, it is believed that a condensation occurs with carbonyl group containing compounds thus yielding a condensate, which is separated from the mixture as described above.

The following examples are provided solely for purposes of illustration and are not intended to limit the scope of the present invention in any manner.

EXAMPLE 1

3.40 g (30.1 mmoles) of ethyl cyanoacetate and 56.60 g of mixed carboxylic acids produced by ozonolysis of oleic acid were heated to 113° C. The mixture was sampled for carbonyl value measurement to provide baseline values. 0.2 g (2 mmoles) octylamine was added and the mixture then sampled periodically for carbonyl value measures. A blank mixture was prepared of mixed carboxylic acids produced by ozonolysis of oleic acid which was heated to 113° C. and sampled periodically for carbonyl value measurement. The resulting carbonyl values are listed below.

| Time | Blank | (mg carboxyl functionality/gm sample) Ethyl Cyanoacetate |
|---|---|---|
| 0 hr. | 5800 | 5800 |
| .25 hr. | 6300 | 3760 |
| .50 hr. | 5330 | 3060 |
| 1.00 hr. | 4990 | 2370 |
| 2.50 hr. | 4720 | 1649 |
| 3.50 hr. | 4519 | 2080 |

7-oxo-octanoic acid used as source of carbonyl for calibration.

EXAMPLE II 1.1703 g (7.40 nmoles) 7-oxo-octanoic acid, 0.8706 g (7.70 mmoles) ethyl cyanoacetate, and 27.9579 g (0.177 moles) nonanoic acid were heated to 120° C. A sample was taken for baseline carbonyl value measurement. 0.029 g (0.22 mmoles) octylamine was added then samples taken periodically for carbonyl value measurement. A blank mixture of 1.1703 g (7.40 mmoles) 7-oxo-octanoic acid and 27.9579 g (0.177 moles) of nonanoic acid was heated to 120° C. and sampled periodically for carbonyl value measurement. The resulting carbonyl values are listed below:

|  | | (mg carboxyl functionality/gm sample) |
| Time | Blank | Ethyl Cyanoacetate |
| --- | --- | --- |
| 0.00 hr. | 7560 | 6760 |
| 0.50 hr. | 7510 | 6150 |
| 1.00 hr. | 7690 | 4940 |
| 2.00 hr. | 7160 | 4880 |
| 4.00 hr. | 6560 | 4050 |
| 20.00 hr. | 7010 | 4060 |

EXAMPLE III 1.0855 g (7.63 mmoles) of nonyl aldehyde, 0.8709 (7.70 mmoles) ethyl cyanoacetate, and 28.0718 g (0.177 moles) nonanoic acid were heated to 120° C. A sample was taken for baseline carbonyl value measurement. 0.02 g (0.2 mmole) octylamine was added and samples were taken periodically for carboxyl value measurement. A blank mixture of 1.0855 g (7.63 mmoles) of nonyl aldehyde and 28.0718 g (0.177 moles) nonanoic acid was heated to 120° C. and sampled periodically for carbonyl value measurement. The resulting carbonyl values are listed below.

|  | | (mg carboxyl functionality/gm sample) |
| Time | Blank | Ethyl Cyanoacetate |
| --- | --- | --- |
| 0.00 hr. | 7560 | 7440 |
| 0.50 hr. | 7510 | 6860 |
| 1.00 hr. | 7670 | 6700 |
| 2.00 hr. | 7160 | 5480 |
| 4.00 hr. | 6560 | 2190 |
| 20.00 hr. | 7010 | 460 |

The examples and embodiments provided above illustrate the present invention. It will be understood that various modifications can be made to the embodiments disclosed herein. For example, the mixtures and compositions described above are generally non-aqueous in nature. It is contemplated that aqueous mixtures may be incorporated when lowering carbonyl values using the techniques disclosed herein. In addition, while the present discussion involves adding catalyst to the carboxylic acid or carboxylic acid derivative containing composition, some catalysts are known to be naturally occurring in such compositions. For example, suitable catalytic amounts of amines may already be present in mixtures of fatty acids, thus reducing or eliminating the need to add additional catalysts. Therefore, the above description should not be construed as limiting, but merely as exemplifications as preferred embodiments. Those skilled in the art will envision other modifications within the scope and spirit of the following claims.

What is claimed is:

1. A process for lowering the carbonyl value of a composition containing one or more fatty acids comprising contacting the composition containing one or more fatty acids with a catalytic amount of a catalyst and an active methylene compound effective to lower the carbonyl value of the composition.

2. A process according to claim 1 wherein the catalyst is selected from the group consisting of amine, ammonia, ammonium salt, titanium tetrachloride, aluminum oxide and combinations thereof.

3. A process according to claim 2 wherein the amine is a primary amine.

4. A process according to claim 2 wherein the amine is a secondary amine.

5. A process according to claim 1 wherein the active methylene compound is represented by the formula X—CH$_2$—Y, wherein X and Y may be the same or different and are electron withdrawing groups.

6. A process according to claim 5 wherein X and Y are selected from the group consisting of

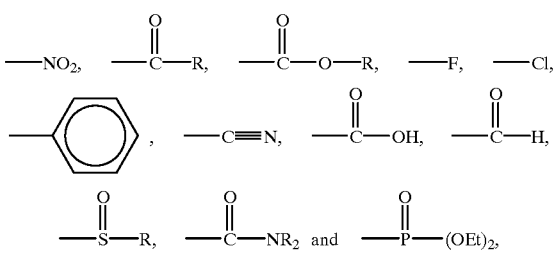

wherein R is the same or different and is alkyl or aryl.

7. A process according to claim 1 wherein the fatty acid is oleic acid or pelargonic acid.

8. A process according to claim 6 wherein the primary amine is n-octylamine.

9. A process according to claim 5 wherein the active methylene compound is cyanoactive methylene.

10. A process according to claim 9 wherein the cyanoactive methylene is cyanoacetic acid or ethylcyanoacetate.

11. A process according to claim 1 wherein the carbonyl value is lowered by formation of condensate.

12. A process according to claim 11 further comprising separating the condensate from the composition.

13. A process according to claim 12 wherein separating is accomplished using a procedure selected from the group consisting of distillation, chromatography and density gradient separation.

14. A process for reducing the amount of carbonyl group containing impurities in a composition including one or more fatty acids comprising contacting the composition containing one or more fatty acids with a catalytic amount of a catalyst and an active methylene compound effective to form a condensate and to reduce the carbonyl value of the composition and separating the condensate from the composition.

15. A process according to claim 14 wherein the catalyst is selected from the group consisting of amine, ammonia, ammonium salt, titanium tetrachloride, aluminum oxide and combinations thereof.

16. A process according to claim 14 wherein the active methylene compound is represented by the formula X—CH$_2$—Y, wherein X and Y may be the same or different and are electron withdrawing groups.

17. A process according to claim 16 wherein the impurities are selected from the group consisting of aldehydes and ketones.

18. A process according to claim 17 wherein the ketone is a keto-acid.

19. A process according to claim 16 wherein the active methylene compound is cyanoactive methylene.

20. A process according to claim 15 wherein the catalyst is a primary amine.

* * * * *